United States Patent
Kudo

(10) Patent No.: US 9,599,844 B2
(45) Date of Patent: Mar. 21, 2017

(54) INSPECTION APPARATUS

(71) Applicant: Kabushiki Kaisha Nihon Micronics, Musashino-shi, Tokyo (JP)

(72) Inventor: Takayoshi Kudo, Musashino (JP)

(73) Assignee: KABUSHIKI KAISHA NIHON MICRONICS, Tokyo (JP)

(*) Notice: Subject to any disclaimer, the term of this patent is extended or adjusted under 35 U.S.C. 154(b) by 170 days.

(21) Appl. No.: 14/521,880

(22) Filed: Oct. 23, 2014

(65) Prior Publication Data
US 2015/0130488 A1    May 14, 2015

(30) Foreign Application Priority Data
Nov. 14, 2013 (JP) .................. 2013-235698

(51) Int. Cl.
| G01R 31/20 | (2006.01) |
| G02F 1/13 | (2006.01) |
| G01N 21/95 | (2006.01) |
| G01N 21/88 | (2006.01) |

(52) U.S. Cl.
CPC ....... *G02F 1/1309* (2013.01); *G01N 21/8803* (2013.01); *G01N 2021/9513* (2013.01)

(58) Field of Classification Search
CPC G01R 31/26; G01R 31/2642; G01R 31/2648; G01R 31/2831; G01R 31/31702; G01R 33/0047; G01R 1/0491; G01R 31/265; G01R 31/3012; G01R 31/318511
See application file for complete search history.

(56) References Cited

U.S. PATENT DOCUMENTS

| 7,098,650 B2* | 8/2006 | Foster ................ G01R 1/07314 |
| | | 324/750.25 |
| 7,295,023 B2* | 11/2007 | Lou ..................... G01R 31/2889 |
| | | 324/750.25 |
| 8,134,381 B2* | 3/2012 | Abe .................... G01R 31/2886 |
| | | 324/754.07 |

FOREIGN PATENT DOCUMENTS

| JP | 2010112919 | 5/2010 |
| TW | 510971 B | 11/2002 |
| TW | 2007-45566 | 12/2007 |
| TW | I396848 B1 | 5/2013 |

OTHER PUBLICATIONS

English translation of relevant part of the Office Action for TW App No. 103137380, dated Apr. 1, 2016, 1 pg.
(Continued)

*Primary Examiner* — Tung X Nguyen
(74) *Attorney, Agent, or Firm* — Procopio, Cory, Hargreaves & Savitch LLP

(57) ABSTRACT

An inspection apparatus capable of reducing the effect of noises is provided. An inspection apparatus according to the present invention includes a work table 26 on which an object, a fixed body 28 disposed above the work table 26, a probe assembly that holds a probe stylus 38a, a support base member 40 supported on the fixed body 28, a suspension mechanism 46 that supports the probe assembly 38 above the work table 26, and a signal circuit substrate 54 including therein an IC chip 54a that generates an inspection signal supplied to the probe stylus 38a, the signal circuit substrate 54 being supported by the suspension mechanism 46 below the suspension mechanism 46, in which the probe assembly 38 and the support base member 40 are electrically isolated from each other.

7 Claims, 13 Drawing Sheets

(56) References Cited

OTHER PUBLICATIONS

TW App. No. 103137380 Office Action issued on Oct. 2, 2015; including English translation of relevant part of the Office Communication.

\* cited by examiner

INSPECTION APPARATUS

INCORPORATION BY REFERENCE

This application is based upon and claims the benefit of priority from Japanese patent application No. 2013-235698, filed on Nov. 14, 2013, the disclosure of which is incorporated herein in its entirety by reference.

BACKGROUND OF THE INVENTION

1. Field of the Invention

The present invention relates to an inspection apparatus.

2. Description of Related Art

Display panels, which have gone through a manufacturing process, usually undergo a lighting inspection for determining whether there are any defects such as pixel defects in the display panels. In this lighting inspection, it is necessary to supply a drive signal to a liquid crystal panel, which is the object to be inspected. Further, a circuit inspection can be performed by performing an array inspection. For example, a drive signal is supplied to a mother glass substrate before it is cut into a plurality of sections. Therefore, the inspection apparatus is provided with, as its inspection station, an electric inspection apparatus including an inspection pedestal on which a liquid crystal panel, which is the object to be inspected, is placed in a state where its electrodes face upward, and a probe unit supported on a fixed frame body disposed above the object to be inspected.

As this type of an electric inspection apparatus, Japanese Unexamined Patent Application Publication No. 2010-112919 discloses an inspection apparatus for a liquid crystal panel. In this inspection apparatus, a rectangular liquid crystal panel, which is an object to be inspected, is placed on an inspection pedestal. A rectangular fixed frame body having sides corresponding to the respective sides of the rectangular liquid crystal panel is disposed above the inspection pedestal. Further, a number of probe assemblies are arranged along a pair of sides adjoining at right angles of the fixed frame body. More specifically, probe stage plates are supported on edges of the fixed frame body. Probe units are attached to the probe stage plates.

Each probe unit includes a support base member and a plurality of probe assemblies. The support base member is fixed to the probe stage plate in a removable fashion. The probe assemblies are supported on the probe stage plates. Each probe assembly is supported on the support base member through its suspension mechanism so that its probes are opposed to corresponding electrodes of a liquid crystal panel. For each suspension mechanism, a signal circuit substrate is supported below that suspension mechanism. A drive signal is supplied to a predetermined probe of the probe assembly through a liquid crystal drive IC circuit composed of an IC chip provided in each signal circuit substrate.

Therefore, in the electric inspection apparatus, the relative position of a liquid crystal panel placed on the inspection pedestal is adjusted so that each electrode provided in that liquid crystal panel is aligned with a respective one of the probes of the probe units supported on the fixed frame body. After this position adjustment, when the tips of the probes of each probe assembly provided in each probe unit come into contact with corresponding electrodes of the liquid crystal panel by the movement of the inspection pedestal toward the fixed frame body, drive signals are sent from predetermined probes to the corresponding electrodes through the IC chip. The liquid crystal panel is brought into a lighting state and maintained in the lighting state for a certain time period by these drive signals, and the liquid crystal panel undergoes a predetermined inspection(s).

In the above-described inspection apparatus, the suspension mechanism is electrically connected to the housing of the prober. Further, the housing is electrically connected to the ground (GND). A current leak could occur due to a capacitive coupling of a probe stylus and a signal circuit substrate. That is, as the housing is connected to the GND, when the GND level fluctuates due to noises caused by the prober or the factory, part of the current of the tester circuit could leak through the capacitive coupling. Therefore, there is a possibility that measurement variations may occur due to these noises.

The present invention has been made in view of the above-described problem, and an object thereof is to provide an inspection apparatus capable of reducing the effect of noises.

SUMMARY OF THE INVENTION

A first exemplary aspect of the present invention is an inspection apparatus including: an inspection pedestal on which an object to be inspected is placed; a fixed body disposed above the inspection pedestal; a probe assembly that holds a probe stylus capable of coming into contact with an electrode of the object; a support base member supported on the fixed body; a suspension mechanism that supports, in the support base member, the probe assembly above the inspection pedestal in order to bring the probe stylus into contact with the electrode; and a signal circuit substrate including therein an electric circuit that generates an inspection signal supplied to the probe stylus, the signal circuit substrate being supported by the suspension mechanism below the suspension mechanism, in which the probe assembly and the support base member are electrically isolated from each other.

In the above-described inspection apparatus, the probe assembly may be electrically isolated from the support base member by interposing an insulating member between the probe assembly and the support base member.

In the above-described inspection apparatus, the probe assembly may be attached to the suspension mechanism through the insulating member interposed therebetween.

In the above-described inspection apparatus, the suspension mechanism may include a suspension base member attached to the support base member and a slide block slidably attached to the suspension base member through a slide mechanism, and the insulating member may be interposed between the slide block and the suspension base member.

In the above-described inspection apparatus, the suspension mechanism may be attached to the support base member through the insulating material interposed therebetween.

The above-described inspection apparatus may further include a housing that houses the inspection pedestal, and the support base member may be electrically connected to ground through the housing.

According to the present invention, it is possible to provide an inspection apparatus capable of reducing the effect of noises.

The above and other objects, features and advantages of the present invention will become more fully understood from the detailed description given hereinbelow and the accompanying drawings which are given by way of illustration only, and thus are not to be considered as limiting the present invention.

DESCRIPTION OF THE EXEMPLARY EMBODIMENTS

Figure 1:
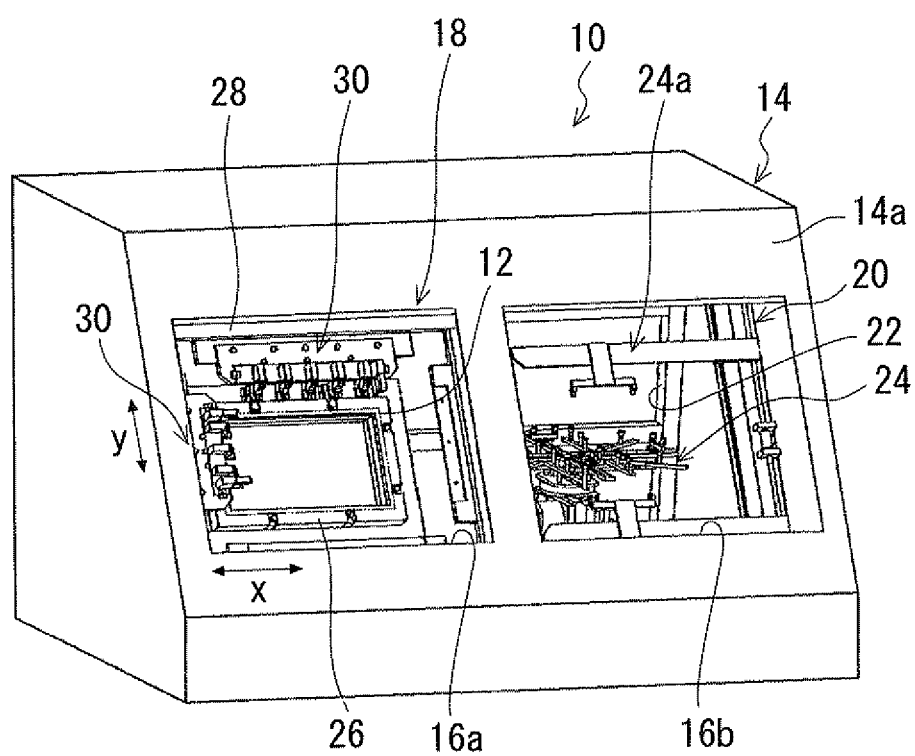
FIG. 1 is a perspective view showing an external appearance of a lighting inspection apparatus according to the present invention.

FIG. 1 shows an external appearance of an inspection apparatus 10 for a panel to be inspected (hereinafter referred to as "inspection panel") according to an aspect of the present invention. This inspection apparatus 10 is used for, for example, a lighting inspection or an array inspection of an inspection panel 12 having a flat rectangular shape as viewed from the top. An example in which the inspection apparatus 10 is used for a lighting inspection is explained hereinafter. The inspection apparatus 10 includes a housing 14 including an inclined front surface 14a. On the inclined front surface 14a of the housing 14, a first window (opening) 16a for a lighting inspection and a second window (opening) 16b adjacent to the first window 16a are formed. The inspection panel 12 is an object to be inspected. For example, the inspection panel 12 is a display panel such as a liquid crystal panel and an organic EL (Electro-Luminescence) panel. Alternatively, the present invention can be applied to a circuit inspection of an X-ray flat panel detector or the like.

Inside the housing 14, an inspection station 18 for the lighting inspection of the inspection panel 12 is provided in a place corresponding to the first window 16a. Inside the housing 14, a panel handover station 20 is also provided next to the inspection station 18. The panel handover station 20 successively hands over/receives inspection panels 12 to/from the inspection station 18. For the panel handover station 20, a conventional well-known configuration can be used. The panel handover station 20 is disposed in a place corresponding to the second window 16b. The housing 14 is electrically connected to the GND (ground).

A number of electrodes 12a (see FIG. 5) are arranged on one of the surfaces of the inspection panel 12. For example, a plurality of electrodes 12a are arranged along one of the long-side edges of the rectangular inspection panel 12. Further, a plurality of electrodes 12a are arranged along one of the short-side edges of the inspection panel 12. As conventionally well-known in this field, the inspection panel 12, which will undergo a lighting inspection in the inspection station 18, is carried into a place on a panel handover apparatus 24 of the panel handover station 20. For example, a conveyance robot (not shown) carries the inspection panel 12 into a place on the panel handover apparatus 24 through an inlet/outlet 22 formed on the rear surface of the housing 14. Note that the inspection panel 12 is carried into a place on the panel handover apparatus 24 in a state where its electrodes 12a face upward. This inspection panel 12 placed on the panel handover apparatus 24 is transferred to the inspection station 18 through a conveyance arm mechanism 24a of the panel handover apparatus 24. Then, a lighting inspection is performed for the inspection panel 12 in the inspection station 18. Further, the inspection panel 12, which has undergone the lighting inspection in the inspection station 18, is transferred back to the panel handover apparatus 24 by means of the conveyance arm mechanism 24a as conventionally well-known in this field. Then, the conveyance robot takes out the inspection panel 12, which has been transferred to the panel handover apparatus 24, from the inspection apparatus 10.

As shown in FIG. 1, the inspection station 18 includes a work table 26 that holds an inspection panel 12 transferred from the panel handover station 20, a rectangular fixed frame body 28 serving as a fixed plate disposed a certain distance away from the work table 26, and a plurality of probe units 30 supported on the fixed frame body 28.

The work table 26 is an inspection pedestal on which the inspection panel 12 is placed. The work table 26 holds the inspection panel 12 in such a manner that the electrodes 12a of the inspection panel 12 face the first window 16a. The inspection panel 12 placed on the work table (inspection pedestal) 26 is held in a place inside the housing 14 corresponding to the first window 16a. The work table 26 is housed inside the housing 14. The work table 26 is supported by an XYZθ-support mechanism (not shown) disposed inside the housing 14. The XYZθ-support mechanism may be one similar to a conventional XYZθ-support mechanism. In this way, the two-dimensional position of the inspection panel 12 on the work table 26 can be adjusted together with the work table 26. That is, the position of the inspection panel 12 can be adjusted in the XYZ-directions. Note that the X-direction and the Y-direction are orthogonal to each other in a plane parallel to the inclined front surface 14a. The Z-direction is orthogonal to the XY-plane. Further, the rotating posture of the inspection panel 12 around the Z-axis, i.e., its angle in the θ-direction can be adjusted.

In a place obliquely above the work table 26, i.e., a place that is located obliquely in front of the work table 26 as viewed from the work table 26 toward the inclined front surface 14a along the Z-axis, the fixed frame body 28 is fixed to the housing 14. For example, the fixed frame body 28, which serves as a fixed body, is disposed a certain distance away from the work table 26.

Figure 2:
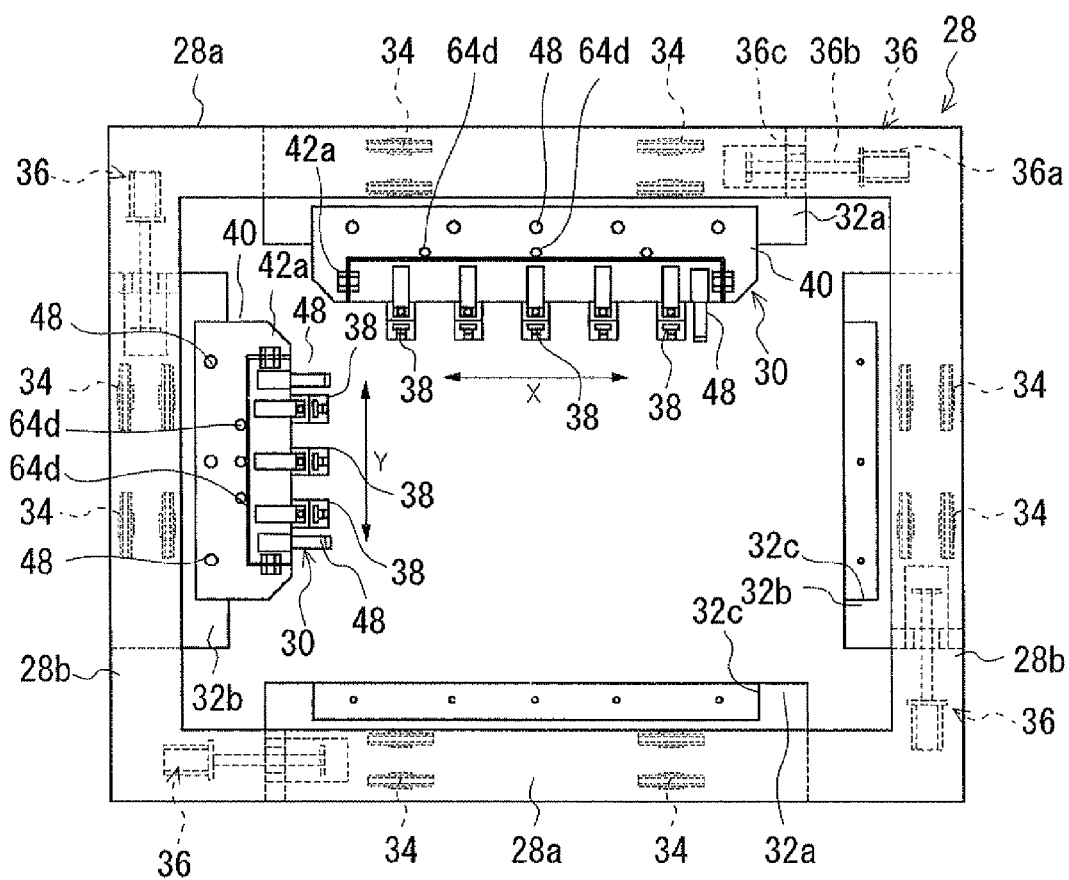
FIG. 2 is a plan view of an inspection stage of the lighting inspection apparatus shown in FIG. 1.

In the example shown in FIG. 2, the fixed frame body 28 has a pair of long side sections 28a extending along the X-direction and a pair of short side sections 28b extending along the Y-direction. That is, the fixed frame body 28 is formed in a rectangular shape. A probe stage plate 32 (32a, 32a, 32b, 32b) is disposed on each of the sides 28a and 28b. A recess 32c for attaching a probe unit 30 is formed on the top surface of each probe stage plate 32. The attachment recess 32c is formed along one of the longitudinal edges of the probe stage plate 32 and has an opened side along that edge. The attachment recess 32c is exposed from the corresponding side 28a or 28b of the fixed frame body 28 toward the inside of the fixed frame body 28. Each probe stage plate 32 is disposed along the corresponding side 28a or 28b. A part of the probe stage plate 32 is disposed in the attachment recess 32c and the remaining part of the probe stage plate 32 protrudes into the inside of the fixed frame body 28.

Guide members 34 are provided between the long side section 28a of the fixed frame body 28 and the probe stage plate 32a. Similarly, guide members 34 are also provided between the short side section 28b of the fixed frame body 28 and the probe stage plate 32b. The probe stage plate 32a is supported on the fixed frame body 28 by the guide members 34 in such a manner that the probe stage plate 32a can move in the longitudinal direction of the long side section 28a. Similarly, the probe stage plate 32b is supported on the fixed frame body 28 by the guide members 34 in such a manner that the probe stage plate 32b can move in the longitudinal direction of the short side section 28b. For example, the probe stage plate 32a moves in the X-direction and the probe stage plate 32b moves in the Y-direction.

Further, a drive mechanism 36 for moving the probe stage plate 32a with respect to the long side section 28a is provided in the long side section 28a. Similarly, a drive mechanism 36 for moving the probe stage plate 32b with respect to the short side section 28b is provided in the short side section 28b. Each of these drive mechanisms 36 may be composed of, for example, an electric motor 36a and a feed mechanism such as a ball screw including a ball screw member 36b and a female screw member 36c. The electric motor 36a is fixed to the fixed frame body 28. The ball screw member 36b can be rotated together with the output shaft of the electric motor 36a in a unified manner. The female screw member 36c is screwed to the ball screw member 36b and thereby fixed to the probe stage plate 32.

In the example shown in FIG. 2, electrodes 12a are arranged along one of the long-side edges and one of the short-side edges of the inspection panel 12. Therefore, a probe unit 30 is attached to the probe stage plate 32a in one of the long side sections 28a corresponding to the electrodes 12a. Similarly, a probe unit 30 is attached to the probe stage plate 32b in one of the short side sections 28b corresponding to the electrodes 12a. The probe unit 30 in the long side section 28a includes five probe assemblies 38 arranged at regular intervals. The probe unit 30 on the short side section 28b includes three probe assemblies 38 arranged at regular intervals.

Each probe unit 30 has substantially the same structure. However, the number of probe assemblies 38 provided in the probe unit in the short side section 28b may be different from that in the long side section 28a. Further, the number of alignment cameras and the number of alignment marks (which will be described later) provided in the probe unit 30 in the short side section 28b may also be different from those provided in the probe unit 30 in the long side section 28a. An example of the probe unit 30 provided in the short side section 28b of the fixed frame body 28 is explained hereinafter. It should be noted that the probe unit 30 in the long side section 28a has a similar configuration.

Figure 3:
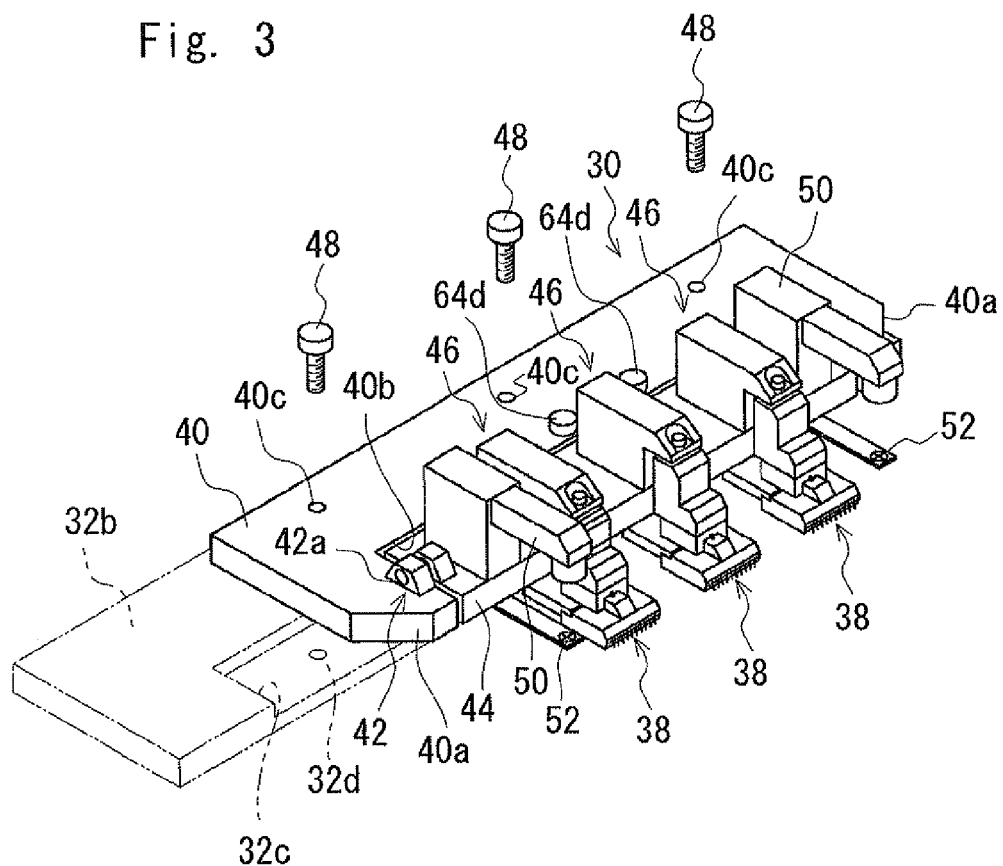
FIG. 3 is a perspective view of a probe unit attached to a probe support member of the lighting inspection apparatus shown in FIG. 2.
Figure 4:
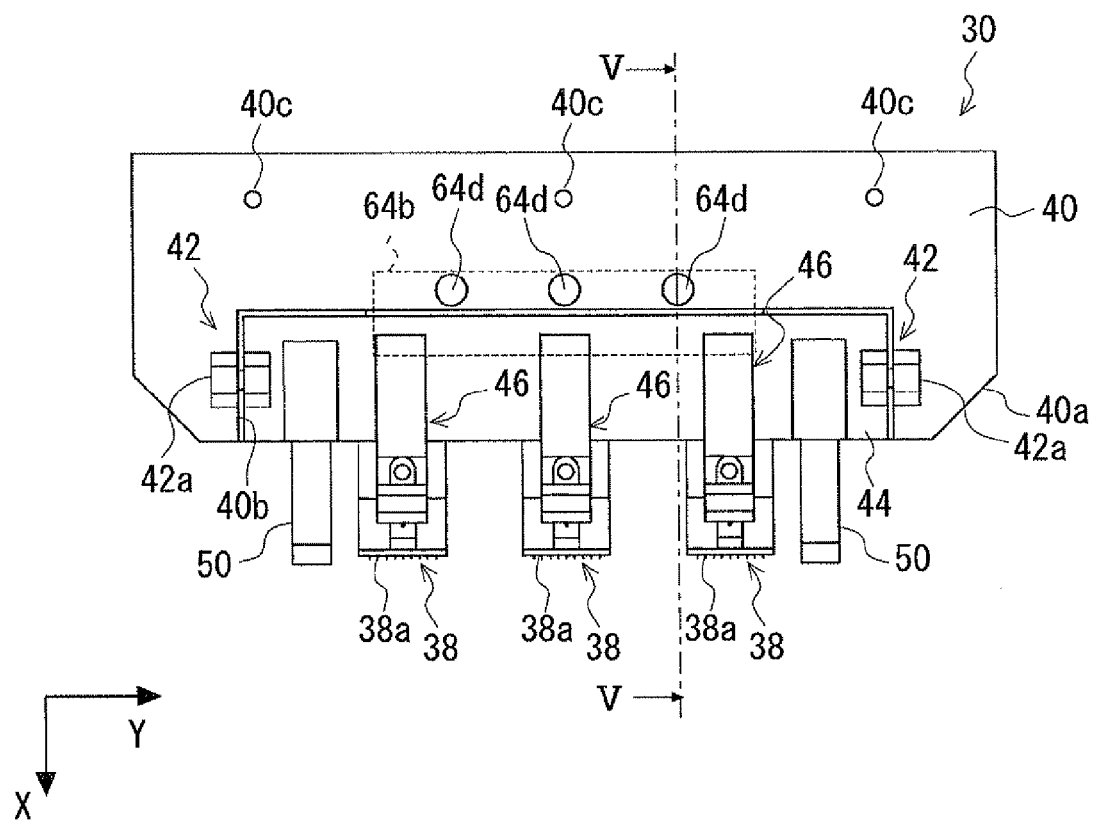
FIG. 4 is a plan view of the probe unit shown in FIG. 3.

As shown in FIGS. 2, 3 and 4, the probe unit 30 includes a support base member 40 having a generally rectangular plate shape, and a probe base plate 44 that is attached to the support base member 40 in such a manner that the probe base plate 44 can rotate around a pair of horizontal shafts 42a of the pivot mechanism 42. Probe assemblies 38 are supported above the probe base plate 44 through their respective suspension mechanisms 46.

The corners between the one of the long sides and the pair of the short sides are chamfered (hereinafter called "chamfered parts 40a"). A cutout section 40b is formed between the chamfered parts 40a formed at both ends of the long side. The cutout section 40b receives the rectangular probe base plate 44 in such a manner that the probe base plate 44 can rotate around the horizontal shafts 42a. As shown in FIG. 3, the edge along the other long side of the support base member 40 is engaged in the attachment recess 32c. In this state, the support base member 40 is fixed to the probe stage plate 32 in a removable fashion. The support base member 40 is fixed to the probe stage plate 32 by using screw members 48 such as bolts. Each screw member 48 passes through a through-hole 40c formed in the support base member 40 and its tip is screwed into a threaded hole 32d formed in the probe stage plate 32b. With this structure, the probe base plate 44 can rotate around the horizontal shafts 42a.

As shown in FIGS. 3 and 4, three probe assemblies 38 are supported above the probe base plate 44 through their respective suspension mechanisms 46. The three probe assemblies 38 are aligned at regular intervals along the longitudinal direction of the probe base plate 44. In the example shown in the figures, a pair of alignment cameras 50 are disposed on both sides of the series of probe assemblies 38. Further, a pair of translucent alignment marks 52, which can be shot by the alignment cameras 50, are disposed below the alignment cameras 50. These pairs of cameras and marks are supported by the probe base plate 44 in such a manner that the series of probe assemblies 38 are disposed therebetween. The alignment cameras 50 take images in which alignment marks (not shown) formed in the inspection panel 12 placed on the work table 26 and the translucent alignment marks 52 supported by the probe base plate 44 are aligned with each other.

Figure 5:
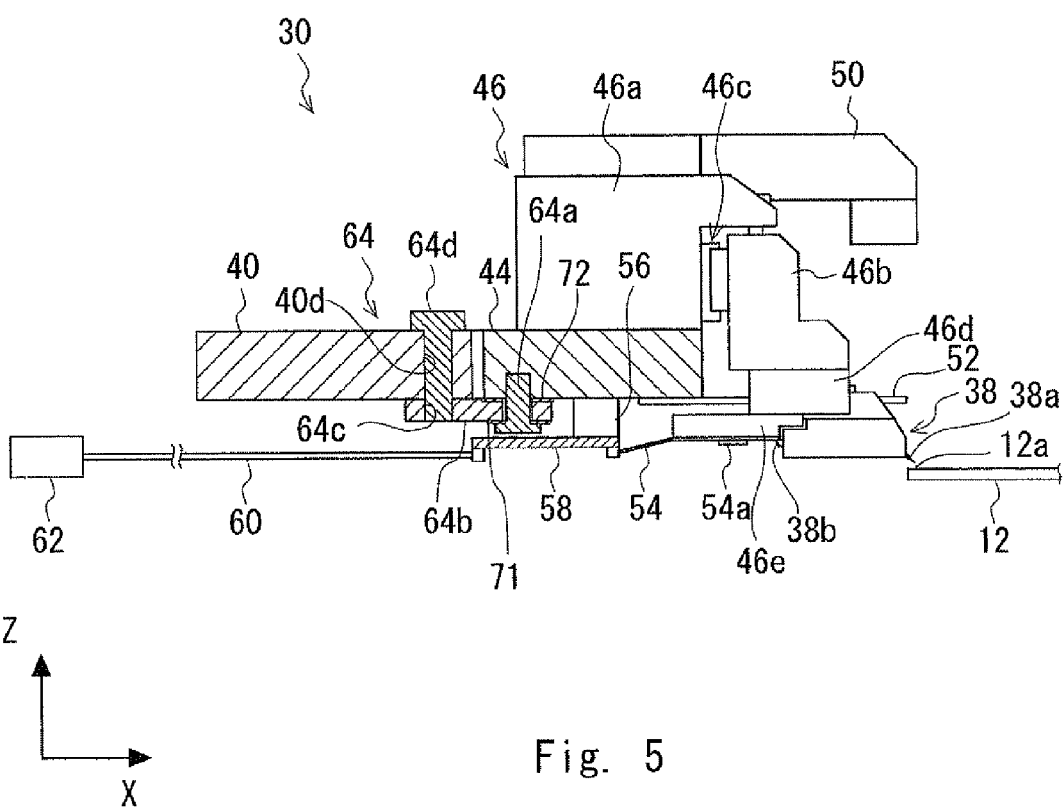
FIG. 5 is a cross section taken along a line V-V in FIG. 4.

The suspension mechanisms 46 are disposed for the corresponding probe assemblies 38. As shown in FIG. 5, each suspension mechanism 46 includes a suspension base member 46a fixed on the probe base plate 44 and a slide block 46b supported by the suspension base member 46a. The slide block 46b can be vertically moved by a linear slide mechanism 46c provided between the slide block 46b and the suspension base member 46a. By using a spring mechanism, the slide block 46b is elastically supported in a suitable manner by the suspension base member 46a without being interfered with by the probe base plate 44. Note that for the spring mechanism (not shown), a conventional well-known structure, which may be incorporated inside the slide block 46b, can be used.

An attachment block 46d for attaching the probe assembly 38 is fixed on the bottom of the slid block 46b. Probe tips (probe styluses) 38a that protrude from the tip of the probe assembly 38 are attached to the probe assembly 38. The probe assembly 38 is attached to the attachment block 46d in a state where the probe tips 38a point downward, i.e., toward the inspection panel 12 placed on the work table 26. In this way, the probe tips 38a come into contact with the corresponding electrodes 12a of the inspection panel 12. The probe assembly 38 serves as a holder that holds a plurality of probe styluses.

Further, an attachment plate 46e is fixed on the bottom of the attachment block 46d. A circuit substrate 54 made of, for example, TCP (Tape Carrier Package) is supported on the bottom surface of the attachment plate 46e. In this circuit substrate 54, a drive signal generation IC chip 54a for generating drive signals (inspection signals) for the inspection panel 12 is mounted and an IC circuit including this IC chip 54a is formed. The probe assembly 38 is attached to the attachment block 46d of the suspension mechanism 46. Then, the rear ends 38b of the probe styluses are pressed from below onto corresponding conductive paths of the circuit substrate 54 so that the probe styluses of the probe assembly 38 receive drive signals. In this way, the probe styluses of the probe assembly 38 are electrically connected to the circuit substrate 54.

The circuit substrate 54 is electrically connected to a relay substrate 58, which is supported on the bottom surface of the probe base plate 44 through a spacer(s) 56 interposed therebetween. This relay substrate 58 is electrically connected to a control signal generator 62 through a line(s) 60. Therefore, the IC chip 54a receives a control signal(s) from the control signal generator 62 through conductive paths of the relay substrate 58 and the circuit substrate 54 and, in response to the control signal, supplies drive signals to corresponding electrodes 12a of the inspection panel 12 through the respective probes. The IC chip 54a converts a digital control signal(s) transmitted through the relay substrate 58 into analog drive signals, and outputs the generated analog drive signals.

A plurality of probe assemblies 38 are attached to the probe base plate 44 through the respective suspension mechanisms 46. As shown in FIG. 5, the probe base plate 44 is fixed to the support base member 40 by joint means 64. The probe base plate 44 has such a posture that the surface of the probe base plate 44 is flush with the surface of the support base member 40.

The joint means 64 includes a bolt 64a, a joint plate 64b, and a bolt 64d. The joint plate 64b is fixed on the bottom surface of the probe base plate 44 by the bolt 64a. The bolt 64d is screwed into a threaded hole 64c formed in the joint plate 64b. A through-hole 40d aligned with the threaded hole 64c is formed in the support base member 40. Therefore, the bolt 64d passes through the through-hole 40d and is screwed into the threaded hole 64c. The bolt 64d passes through the through-hole 40d from the top surface of the support base member 40. Then, the joint plate 64b is tightened to the support base member 40 so that the tip of the bolt 64d is screwed in the threaded hole 64c. This tightening of the bolt 64d prevents the probe base plate 44 from rotating around the horizontal shafts 42a. As a result, the probe base plate 44 is held in the posture shown in FIG. 5 as described previously.

Alternatively, other structures may be used instead of using the above-described structure in which the joint plate 64b with the threaded hole 64c formed therein is fixed to the probe base plate 44 by the bolt 64a. For example, though its illustration in the figures is omitted, an extension member that is integrally formed with the probe base plate 44 and extends downward from the probe base plate 44 may be used instead of using the joint member with the threaded hole 64c formed therein.

Further, insulating members 71 and 72 are provided in the joint means 64. Therefore, the joint means 64 fixes the suspension mechanism 46 to the probe base plate 44 while electrically isolating the suspension mechanism 46 and the support base member 40 from each other. Note that details of this structure are described later.

In the inspection apparatus 10 according to an aspect of the present invention, a probe unit(s) 30 that conforms to the specifications of the inspection panel 12, which is the object to be inspected, is selected. That is, a probe assembly(s) 38 having appropriate probe intervals corresponding to the intervals at which the electrodes 12a of the inspection panel 12 are arranged are used. Further, a probe unit 30 including a plurality of probe assemblies 38 arranged at predetermined intervals is used. Further, an appropriate probe unit 30 is attached to the probe stage plate 32.

After that, an inspection panel 12 is transferred from the panel handover station 20 onto the work table 26 of the inspection station 18. Then, an XYZθ-support mechanism aligns the electrodes 12a with the corresponding probe tips 38a of the probe assemblies 38 based on the deviation between the translucent alignment marks 52 and the alignment marks on the inspection panel 12 observed on an image(s) taken by the alignment cameras 50. That is, the position of the work table 26 is appropriately adjusted. Further, the position of each probe stage plate 32 to which the respective probe unit 30 is attached is finely adjusted by the drive mechanism 36.

After these adjustments, the work table 26 is moved toward the fixed frame body 28 by the operation of the XYZθ-support mechanism. By doing so, the electrodes 12a of the inspection panel 12 are electrically connected to the probe tips 38a of the probe assemblies 38. In this connected state, drive signals are supplied from the IC chip 54a to the inspection panel 12 through the corresponding probes. As a result, the inspection panel 12 is lighted according to these drive signals. A worker or an operator observes this lighting state through the first window 16a and thereby carries out a lighting inspection.

Figure 6:
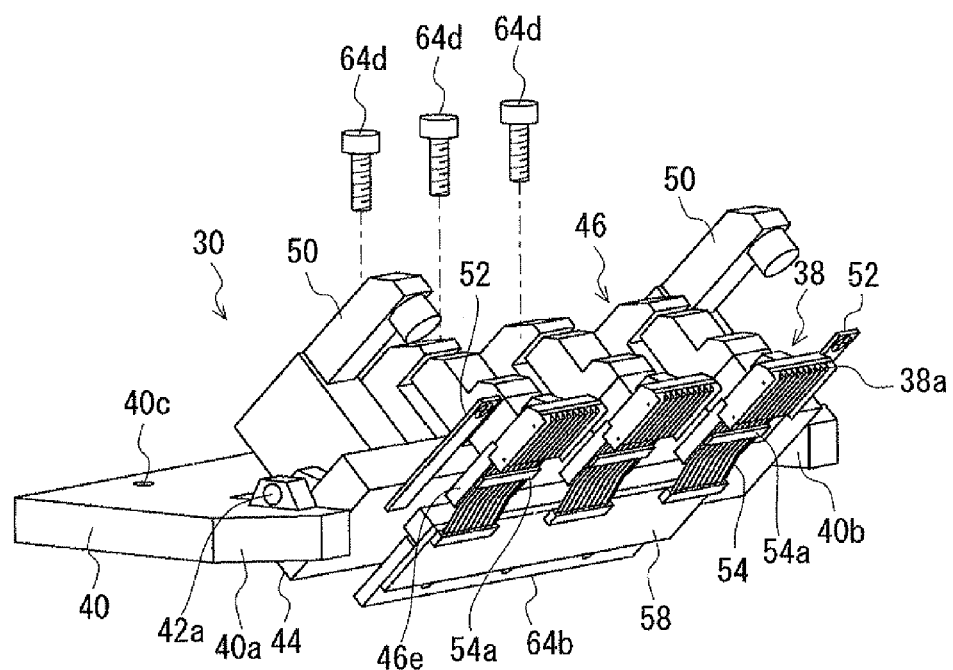
FIG. 6 is a perspective view showing a probe unit according to the present invention when it is in an inclined state.

In a maintenance inspection of the circuit substrate 54 disposed in the inspection apparatus 10 according to an aspect of the present invention, the bolts 64d, which are screwed into the threaded holes 64c of the joint plate 64b of the joint means 64, are loosened as shown FIG. 5. Then, as shown in FIG. 6, the bolts 64d are pulled out from the joint plate 64b. By doing so, the joint means 64 is disengaged.

By this disengagement of the joint means 64, the probe base plate 44 is rotated around the horizontal shafts 42a with respect to the support base member 40. Therefore, the probe assemblies 38, the alignment cameras 50, and so on supported above the probe base plate 44 through suspension mechanism 46 are also rotated. The circuit substrate 54, which is disposed below the suspension mechanism 46, is turned toward the first window 16a.

By this rotation of the posture of the probe base plate 44, the circuit substrate 54 and its IC chip 54a are exposed toward the first window 16a. Therefore, a worker or an operator can carry out work such as the inspection and/or the replacement of the IC chip 54a through the first window 16a without inserting his/her hand through the gap between the work table 26 and the fixed frame body 28. Further, the worker or operator can carry out inspections and replacements without removing or separating the heavy probe units 30 from the respective probe stage plates 32. Therefore, the worker or operator can carry out inspections and replacements more easily in a more comfortable posture than when they carry out those tasks in the conventional fashion.

It is conceivable that the circuit substrate 54 can be disposed on the top surface of the probe base plate 44 or the top surface of the support base member 40 so that the maintenance inspection of the circuit substrate 54 can be easily carried out. As a result, however, the length of the connection paths between the IC chip 54*a* and the probes of the probe assemblies 38 increases. Therefore, this configuration is undesirable in terms of the noise in consideration of the fact that high frequency signals flow through these connection paths.

In contrast to this, according to the inspection apparatus 10 in accordance with an aspect of the present invention, since the circuit substrate 54 can be held near the probe assemblies 38 below the suspension mechanisms 46, an increase in the connection distance between the IC chip 54*a* and the probe assemblies 38 is prevented. Therefore, the maintenance inspection work for the circuit substrate 54 can be easily carried out without causing the above-described noise problem.

Figure 7:
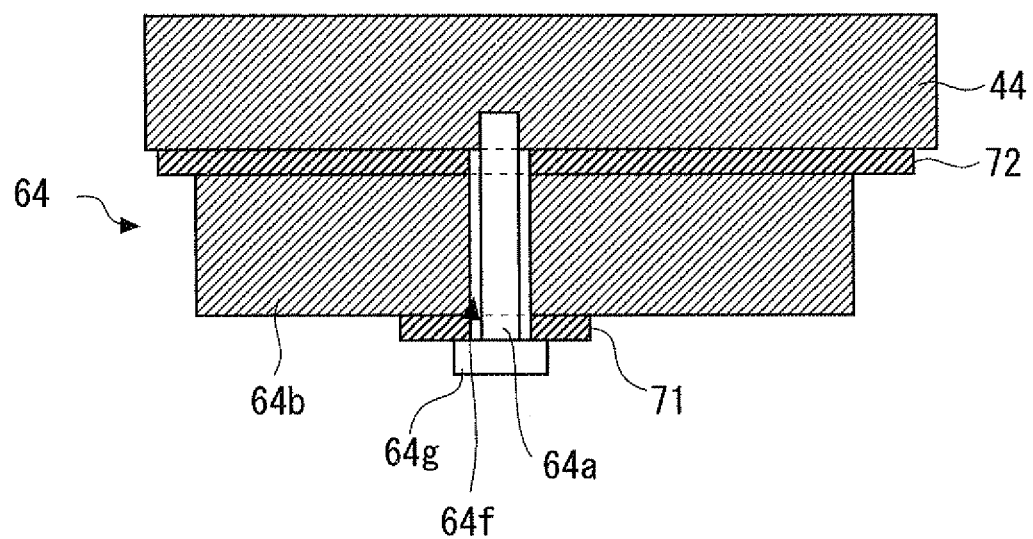
FIG. 7 schematically shows an insulating structure of a probe assembly.

The joint mechanism by the joint means 64 is explained hereinafter with reference to FIG. 7. FIG. 7 is a cross section schematically showing the joint section between the joint means 64 and the probe base plate 44. The insulating member 72 is disposed over the joint plate 64*b* and the insulating member 71 is disposed under the joint plate 64*b*.

The insulating member 72 is interposed between the probe base plate 44 and the joint plate 64*b*. The insulating member 72 is an insulating plate with a through-hole formed therein. The bolt 64*a* passes through this through-hole. Further, the bolt 64*a* also passes through the through-hole 64*f* of the joint plate 64*b*. The insulating member 71 is disposed between the head 64*g* of the bolt 64*a* and the joint plate 64*b*. The insulating member 71 is an insulating washer fixed between the head 64*g* and the joint plate 64*b* by the bolt 64*a*. The bolt 64*a* passes through the insulating member 71, the joint plate 64*b*, and the insulating member 72, and is screwed into the threaded hole formed in the probe base plate 44. Each of the insulating members 71 and 72 is formed of an insulating material such as a plastic, acryl, a fluorocarbon resin, Teflon (registered trademark), vinyl chloride, rubber, a glass epoxy resin, a phenolic resin, ceramics, and glass. The bolt 64*a* is not in contact with the joint plate 64*b*.

By disposing the insulating members 71 and 72 as shown above, the probe base plate 44 can be fixed to the support base member 40 while electrically isolating the joint plate 64*b* and the probe base plate 44 from each other. Note that although the insulating members 71 and 72 are used for the bolt 64*a* in the above explanation, a similar insulating member(s) can be disposed for the bolt 64*d*. In such a configuration, the suspension mechanism 46 can also be fixed while electrically isolating the joint plate 64*b* and the support base member 40 from each other.

By interposing the insulating members 71 and 72 between the probe assemblies 38 and the support base member 40, the probe assemblies 38 can be electrically isolated from the support base member 40. Therefore, even when the probe base plate 44 is connected to the housing 14 and thereby connected to the GND, the effect of noises can be reduced. For example, it is possible to prevent noises caused in the factory from affecting the tester circuit through the housing 14.

Figure 8:
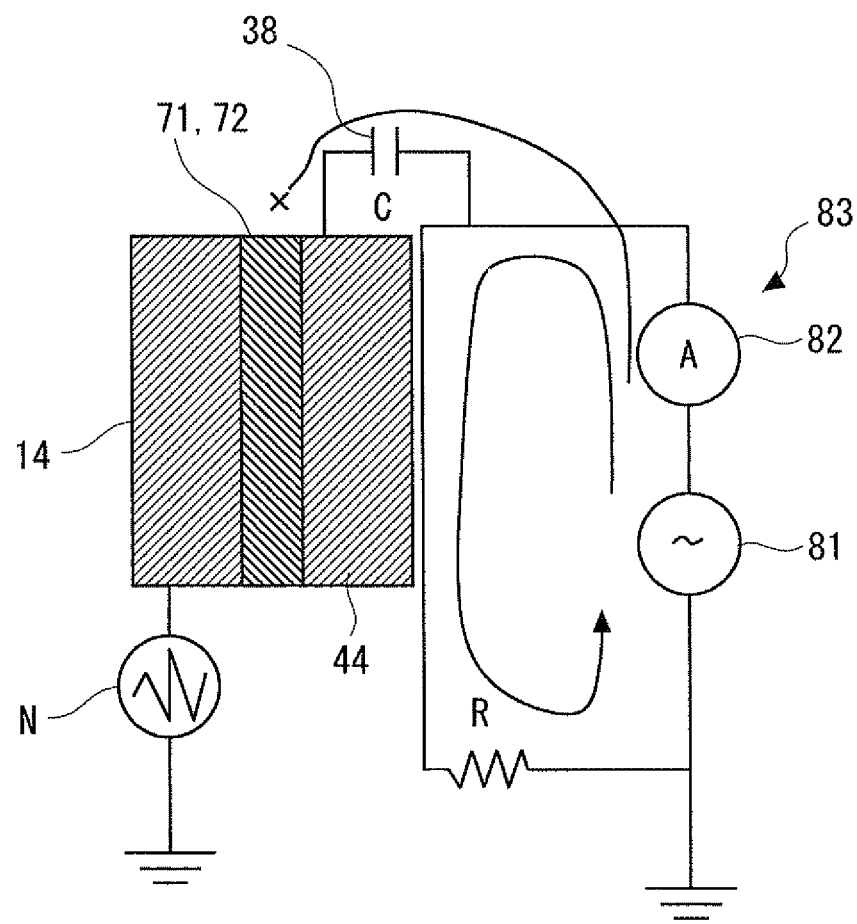
FIG. 8 is a figure for explaining noises in a configuration in which a probe assembly is electrically isolated.
Figure 9:
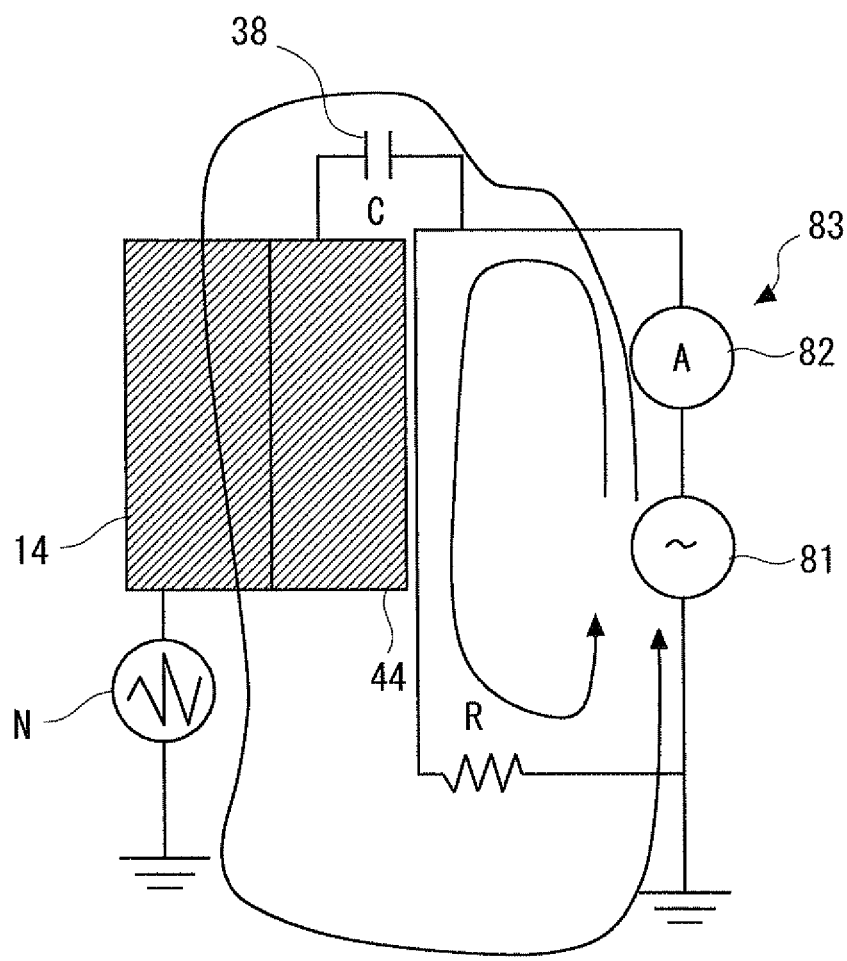
FIG. 9 is a figure for explaining noises in a comparison example in which probe assemblies are not electrically isolated.

The effect of noises is explained hereinafter with reference to FIGS. 8 and 9. FIG. 8 is an imaginary circuit diagram showing a configuration in which the suspension mechanism 46 is electrically isolated from the support base member 40 as in the case of this exemplary embodiment. FIG. 9 is a circuit diagram schematically showing a comparative example in which the suspension mechanism 46 is not electrically isolated from the support base member 40.

As shown in FIG. 8, a measurement current is supplied from a power supply 81 to a tester circuit 83. Note that the tester circuit 83 is a circuit including a probe tip (probe stylus) 38*a*, a circuit substrate 54, an IC chip 54*a*, and so on. An ammeter 82 measures a measurement current flowing through a resistor R of the tester circuit 83. In this way, an inspection panel 12*a* is inspected.

Note that the tester circuit 83 is capacitive-coupled with the suspension mechanism 46. That is, a stray capacitance C is formed by the tester circuit 83 and the suspension mechanism 46. Specifically, when the probe tip (probe stylus) 38*a* or wiring of the circuit substrate 54 is disposed near the conductive suspension mechanism 46, a stray capacitance C occurs.

In this exemplary embodiment, the suspension mechanism 46 and the support base member 40 are electrically isolated by the insulating members 71 and 72 as shown in FIGS. 5 and 7. Therefore, even when a noise N occurs in the ground of the housing 14, the leak current, which would otherwise leak from the tester circuit 83 through the housing 14 and the support base member 40, can be suppressed. Therefore, according to the configuration of this exemplary embodiment, the effect of noises that occur in analog signals can be reduced.

The IC chip 54*a* converts a digital signal(s) generated by the control signal generator 62 into analog signals, and outputs the generated analog signals to the probe tips 38*a*. In this process, if noises occur between the IC chip 54*a* and the probe tip 38*a*, those noises will have a large effect on the measurement data. Further, if there is a part in the wiring of the circuit substrate 54 or the probe tips 38*a* that is disposed very close to the metal part of the suspension mechanism 46, the stray capacitance C becomes larger. By electrically isolating the parts disposed near the circuit substrate 54 or the probe tips 38*a* from the housing 14, the effect of noises can be effectively suppressed. In particular, it is preferable to electrically isolate the probe assembly 38, the attachment plate 46*e*, the attachment block 46*d*, and so on that are located near the circuit substrate 54 from the support base member 40.

On the other hand, when the probe assembly 38 and the housing 14 are not electrically isolated from each other as shown in the comparative example shown in FIG. 9, part of the measurement current flowing in the tester circuit 83 flows to the ground side through the capacitive coupling. Therefore, when a noise N occurs in the ground of the housing 14, a current leaks from the tester circuit 83.

As described above, current leaks caused by noises N can be suppressed in this exemplary embodiment. In this way, it is possible to perform an inspection under a low-noise environment. Therefore, an inspection can be performed without increasing the number of samplings for the measurement, which would otherwise be necessary to average noise effect. Consequently, measurement can be performed in a short time. Further, it is possible to prevent such a situation that a noise greater than the permissible level occurs and prevents a desired measurement result from being obtained, thus enabling an accurate inspection.

Although the insulating members 71 and 72 are provided in the joint means 64 for joining the probe base plate 44 with support base member 40 in the above explanation, the electrical isolation may be achieved in other parts of the probe unit 38. That is, the electrically isolated place is not limited to the place between the joint plate 64*b* and the probe base plate 44. Modified examples in which the electrically isolated place is changed from that of the above-described example are explained hereinafter. Note that explanations of the parts that are the same as those in the above-described exemplary embodiments are omitted in the following explanations of the modified examples.

First Modified Example

Figure 10:
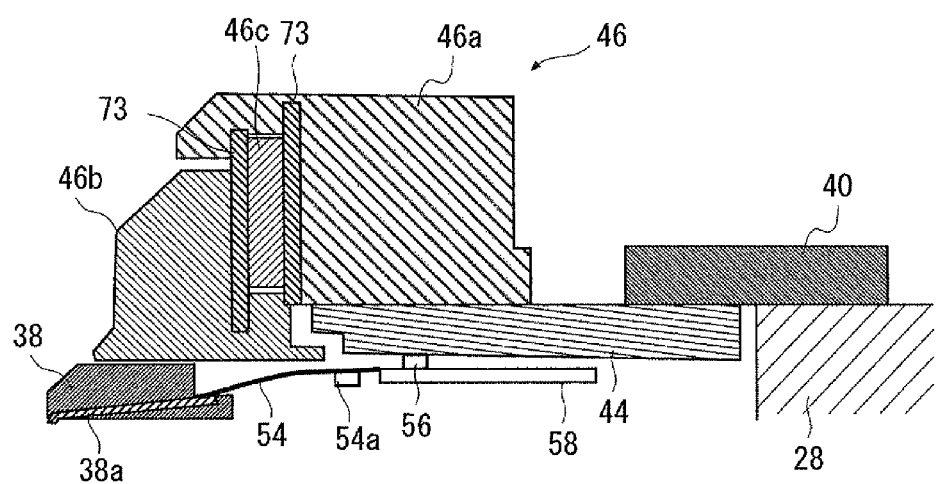
FIG. 10 shows a first modified example of an insulating part.

FIG. 10 schematically shows a first modified example. Note that parts of the configuration of the suspension mechanism 46 and so on are illustrated in a simplified manner in FIG. 10. In the first modified example, an insulating member 73 is provided in the linear slide mechanism 46c. The insulating member 73 is interposed between the slide block 46b and the suspension base member 46a. The linear slide mechanism 46c is attached to the suspension base member 46a through the insulating member 73 interposed therebetween. The slide block 46d is attached to the linear slide mechanism 46c through the insulating member 73 interposed therebetween. In this configuration, the probe assembly 38 is also electrically isolated from the support base member 40. Therefore, an advantageous effect similar to the above-described advantageous effect can be achieved.

Second Modified Example

Figure 11:
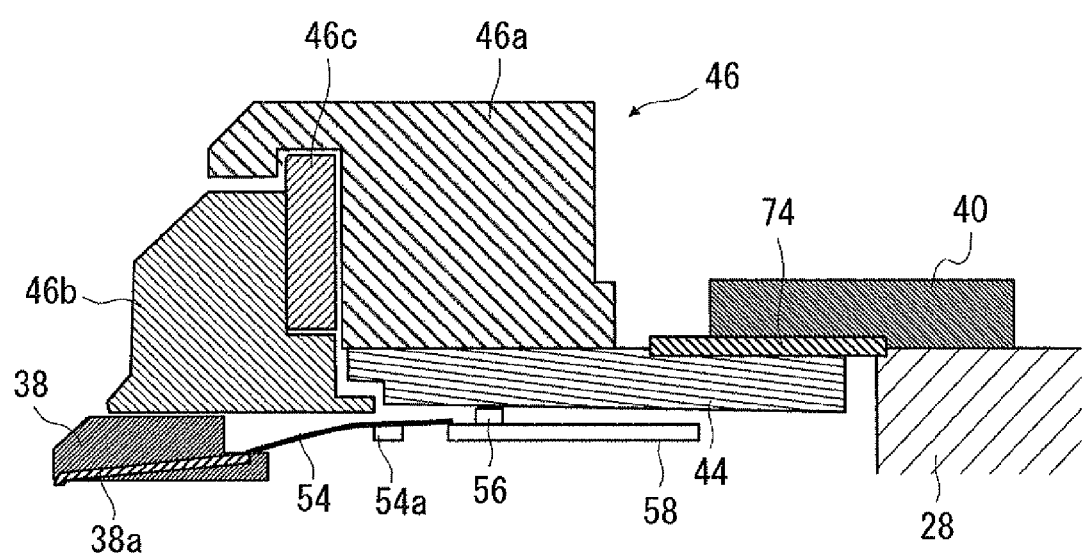
FIG. 11 shows a second modified example of the insulating part.

FIG. 11 schematically shows a second modified example. Note that parts of the configuration of the suspension mechanism 46 and so on are illustrated in a simplified manner in FIG. 11. In the second modified example, an insulating member 74 is provided between the probe base plate 44 and the support base member 40. That is, the probe base plate 44 is attached to the support base member 40 through the insulating member 74 interposed therebetween. In this configuration, the probe assembly 38 is also electrically isolated from the support base member 40. Therefore, an advantageous effect similar to the above-described advantageous effect can be achieved.

Third Modified Example

Figure 12:
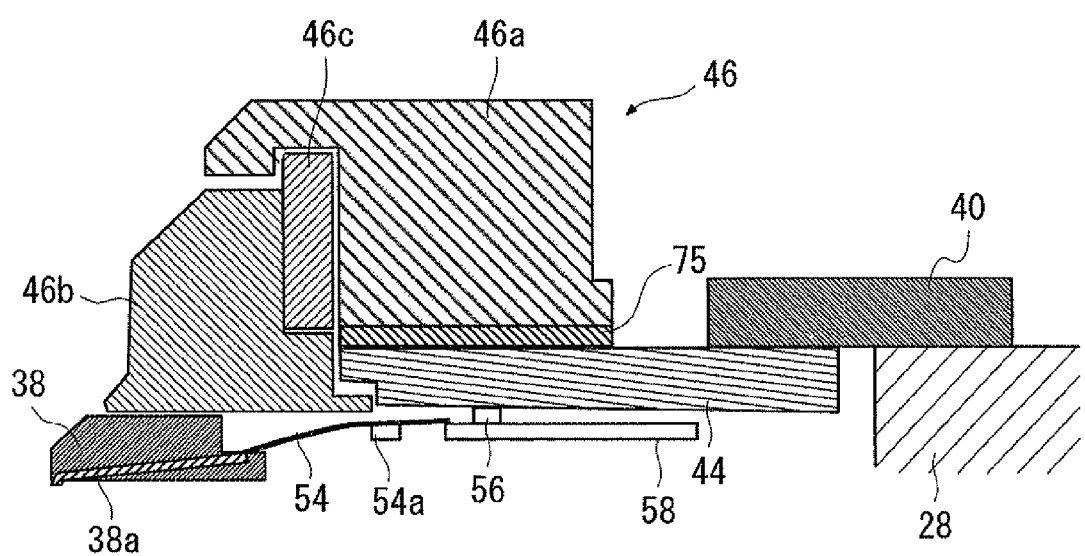
FIG. 12 shows a third modified example of the insulating part.

FIG. 12 schematically shows a third modified example. Note that parts of the configuration of the suspension mechanism 46 and so on are illustrated in a simplified manner in FIG. 12. In the third modified example, an insulating member 75 is provided between the probe base plate 44 and the suspension mechanism 46. That is, the probe base plate 44 is attached to the support base member 40 through the insulating member 75 interposed therebetween. In this configuration, the probe assembly 38 is also electrically isolated from the support base member 40. Therefore, an advantageous effect similar to the above-described advantageous effect can be achieved.

Fourth Modified Example

Figure 13:
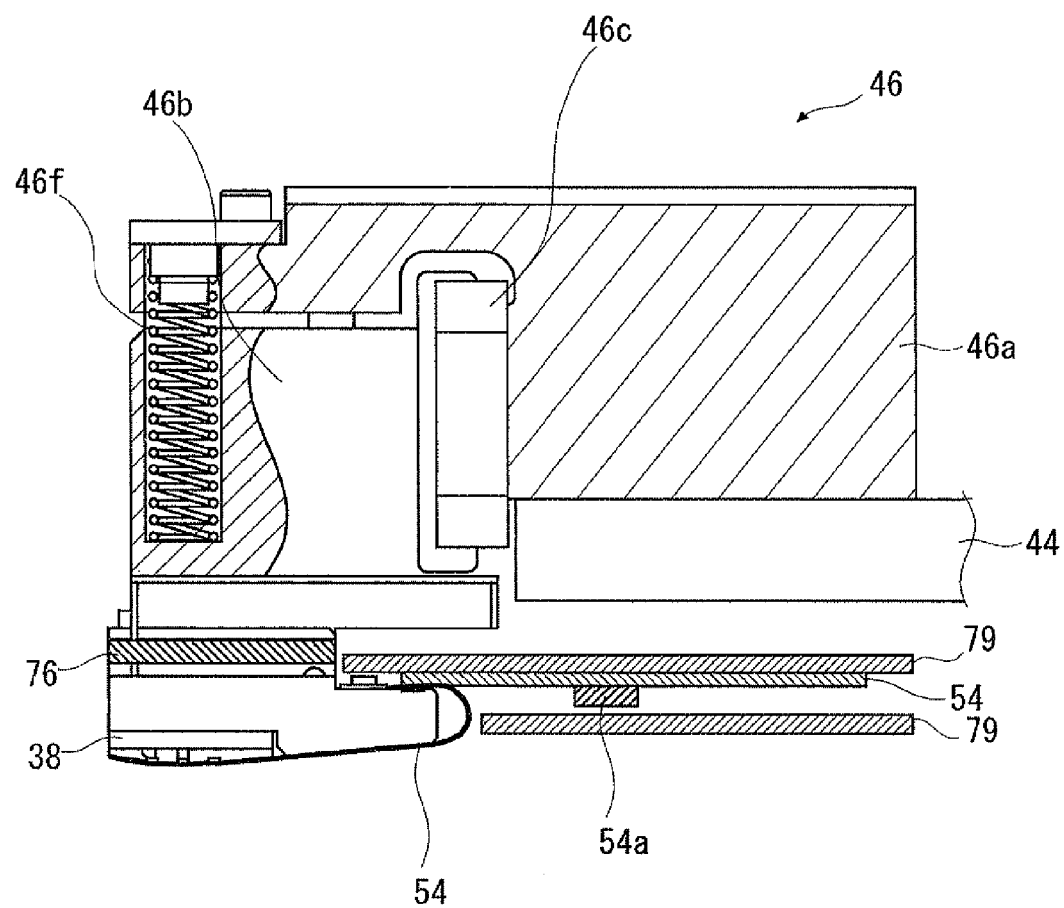
FIG. 13 shows a fourth modified example of the insulating part.

FIG. 13 schematically shows a fourth modified example. Note that parts of the configuration of the suspension mechanism 46 and so on are illustrated in a simplified manner in FIG. 13. Further, in the fourth modified example, radiator plates 79 are disposed above and below the circuit substrate 54. A spring mechanism 46f is provided between the slide block 46b and the suspension base member 46a. Therefore, as described previously, the slide block 46b is elastically supported in a suitable manner by the suspension base member 46a without being interfered with by the probe base plate 44.

In the fourth modified example, an insulating member 76 is disposed between the probe assembly 38 and the slide block 46b. That is, the probe assembly 38 is attached to the suspension mechanism 46 through the insulating member 76 interposed therebetween. In this configuration, the probe assembly 38 is also electrically isolated from the support base member 40. Therefore, an advantageous effect similar to the above-described advantageous effect can be achieved.

As described above, the probe assembly 38 can also be electrically isolated from the housing 14 in the configurations of the first to fourth modified examples. For the fixing of the insulating members in the first to fourth modified examples, a structure similar to that shown in FIG. 7 may be used. Needless to say, the screw or the bolt itself may be formed of insulating material.

Further, at least two of the first exemplary embodiment and first to fourth modified examples may be combined. That is, two or more insulated places are provided to electrically isolate the probe assembly 38 and the support base member 40 from each other. In such cases, insulating members are disposed in two or more places. Further, the insulated places are preferably located near the probe assembly 38. For example, the noise reduction effect in the configuration of the fourth modified example is better than that in the configuration of the second modified example.

Although the inspection apparatus 10 that performs a lighting inspection for the inspection panel 12 such as a liquid crystal panel is explained in the above explanation, this exemplary embodiment can also be applied to inspection apparatuses that perform inspections other than the lighting inspection. For example, an array inspection can be performed for a TFT substrate of a liquid crystal panel. By performing an array inspection, a circuit(s) provided in the inspection panel 12 can be inspected. For example, in the array inspection, an inspection apparatus supplies drive signals to a mother glass substrate through probes 38a before the mother glass substrate is cut into a plurality of sections. Further, an array inspection for a circuit(s) can also be performed for a detector panel such as an XRAY flat panel detector by using a technique similar to the above one.

Although exemplary embodiments according to the present invention have been explained above, the present invention also includes various modifications that do not substantially impair the purposes and the advantages of the present invention. Further, the above-described exemplary embodiments should not be used to limit the scope of the present invention.

From the invention thus described, it will be obvious that the embodiments of the invention may be varied in many ways. Such variations are not to be regarded as a departure from the spirit and scope of the invention, and all such modifications as would be obvious to one skilled in the art are intended for inclusion within the scope of the following claims.

What is claimed is:
1. An inspection apparatus comprising:
an inspection pedestal on which an object to be inspected is placed;
a fixed body disposed above the inspection pedestal;
a plurality of probe assemblies, each of the probe assemblies holding a probe stylus capable of coming into contact with an electrode of the object;
a support base member supported on the fixed body;
a plurality of suspension mechanisms, each of the suspension mechanisms supporting, in the support base member, the probe assembly above the inspection pedestal in order to bring the probe stylus into contact with the electrode;

a probe base plate that supports the probe assembly through the suspension mechanism and is attached to the support base member through a shaft, wherein the probe base plate rotates around the shaft, and a signal circuit substrate comprising therein an electric circuit that generates an inspection signal supplied to the probe stylus, the signal circuit substrate being supported by each of the suspension mechanisms below each of the suspension mechanisms, wherein each of the probe assemblies and their respective support base members are electrically isolated from each other.

2. The inspection apparatus according to claim 1, wherein the plurality of probe assemblies are electrically isolated from the support base member by interposing an insulating member between the plurality of probe assemblies and the support base member.

3. The inspection apparatus according to claim 2, wherein the plurality of probe assemblies are attached to the plurality of suspension mechanisms through the insulating member interposed therebetween.

4. The inspection apparatus according to claim 1, wherein each of the plurality of suspension mechanisms comprises:

a suspension base member attached to the support base member; and a slide block slidably attached to the suspension base member through a slide mechanism, and the plurality of probe assemblies are electrically isolated from the support base member by interposing an insulating member between the slide block and the suspension base member.

5. The inspection apparatus according to claim 1, wherein the plurality of probe assemblies are electrically isolated from the support base member by attaching the respective plurality of suspension mechanisms to the support base member through an insulating member interposed therebetween.

6. The inspection apparatus according to claim 2, wherein the insulating member is provided in at least two places.

7. The inspection apparatus according to claim 1, further comprising a housing that houses the inspection pedestal, wherein the support base member is electrically connected to ground through the housing.

* * * * *